(12) United States Patent
Chang et al.

(10) Patent No.: US 7,164,010 B1
(45) Date of Patent: Jan. 16, 2007

(54) MOLECULAR MAGNETIC PROTEIN

(75) Inventors: Chia-Ching Chang, Hsinchu (TW);
Lou-Sing Kan, Baltimore, MD (US);
Shang-Fan Lee, Taipei (TW);
Ken-Wen Sun, Taichung (TW)

(73) Assignee: Academia Sinica, Taipei (TW)

( * ) Notice: Subject to any disclaimer, the term of this patent is extended or adjusted under 35 U.S.C. 154(b) by 0 days.

(21) Appl. No.: 11/237,160

(22) Filed: Sep. 28, 2005

(51) Int. Cl.
*C07K 14/825* (2006.01)
*A61K 38/00* (2006.01)

(52) U.S. Cl. .................. 530/400; 530/355; 514/2; 424/493; 424/498

(58) Field of Classification Search ............... 530/400, 530/355; 514/2; 424/493, 498
See application file for complete search history.

(56) References Cited

U.S. PATENT DOCUMENTS 5,672,687 A   9/1997   Hermentin et al.
6,262,306 B1  7/2001   Leriche et al.

FOREIGN PATENT DOCUMENTS

JP   2002-260907   9/2002

OTHER PUBLICATIONS

Chang et al. (2006) Mn, Cd-metallothionein-2: a room temperature magnetic protein. Biochem. Biophys. Res. Commun. vol. 340, No. 4, pp. 1134-1138.*
Ejnik et al. (1999) Interprotein metal ion exchange between cadmium-carbonic anhydrase and apo- or zinc-metallothionein. J. Biol. Inorg. Chem. vol. 4, No. 6, pp. 784-790.*
Palumaa et al. (2005) Metal binding of metallothionein-3 versus metallothionein-2: lower affinity and higher plasticity. Biochim. Biophys. Acta. vol. 1747, issue 2, pp. 205-211.*
Vasak, M. (1991) Metal removal and substitution in vertebrate and invertebrate metallothiothioneins. Methods Enzymol. vol. 205, pp. 452-458.*
Kamilla et al. (2002) New semiconductor materials for magnetoelectronics at room temperature, Bull. Mater. Sci., vol. 25, No. 6, pp. 541-543.*
Y. L. Liu et al., Reversible folding of cysteine-rich metallothionein by an over critical reaction path, *Biochem. Biophy Res. Comm.*, vol. 306 pp. 59-63 (2003).
J. D. Otvos et al., Structure of the metal clusters in rabbit live metallothionein, *Proc. Natl. Acad. Sci.*, vol. 77, No. 12 pp. 7094-7098 (1980).
Y Boulanger et al., Model for mammalian metallothionein structure, *Proc. Natl. Acad. Sci.*, vol. 80, pp. 1501-1505 (1983).

Nicola Spaldin, Magnetic materials: Fundamentals and device applications, *Cambridge University Press*, (2003).
C.C. Chang et al., Semi-empirical simulation of Zn/Cd binding site preference in the metal binding domains of mammalian metallothionein, *Protein Engineering*, vol. 9, No. 12 pp. 1165-1172 (1996).
A. H. Robbins et al., Refined Crystal Structure of Cd, Zn Metallothionein at 2.0 A Resolution, *J. Mol. Biol. vol. 221*, pp. 1269-1293 (1991).
D. L. Eaton, Short Communications: Effects of Various Trace Metals on the Binding of Cadmium to Rat hepatic Metallothionein Determined by the Cd/Hemoglobin Affinity Assay, *Toxicol. Appl. Pharmacol.* vol. 78, pp. 158-162 (1985).
S. Wei et al., Alloy-Stabilized Semiconducting and Magnetic zinc-Blende Phase of MnTe, *Phys. Rev. Lett.*, vol. 56 No. 22, pp. 2391-2394 (1986).
B. Messerle et al., Comparison of the Solution Conformations of Human [$Zn_7$]-metallothionein-2 and [$Cd_7$]-metallothionein-2 usng Nuclear Magnetic Resonance Spectroscopy, *J. Mol. Biol.*, vol. 225 pp. 433-443 (1992).
W. Prellier et al., Oxide-diluted magnetic semiconductors: a review of the experimental status, *J. Phys.: Condensed Matter*, vol. 15 pp. R1583-R1601 (2003).
B. Lunn et al., Multiple quantum well structures containing the dilute magnetic semiconductor $Cd_{1-x}Mn_xTe$ grown by molecular beam epitaxy on InSb, Semicond. Sci. Technol. vol. 5, pp. 1155-1160 (1990).
M. de Naurois et al., High resolution x-ray diffraction studies of short-period CdTe/MnTe superlattices, J. Appl. Phys. vol. 81, pp. 6120-6125 (1997).
S.N. Khanna et al., Quantum Phenomena in Clusters an Nanostructures, ISBN:3-540-00015-1.
Petty, Bryce & Bloor, Introduction to molecular electronics, molecular magnets, London: Edward Arnold, ISBN:0340580097(1995).
O. Kahn, Magnetism of the heteropolymetallic systems, *Struct Bonding* (Berlin) vol. 68, pp. 89-167 (1987).

* cited by examiner

*Primary Examiner*—Jon Weber
*Assistant Examiner*—Samuel W. Liu
(74) *Attorney, Agent, or Firm*—Cohen, Pontani, Lieberman & Pavane

(57) ABSTRACT

A highly magnetically aligned metallothionein (MT) containing manganese (Mn) and cadmium (Cd) has been synthesized. The metallotionein has a formula of $Mn_x Cd_{7-x}$ MT with x being in the range of 1 to 6. Its size and biological functions are similar as those of the native metallothionein as tested by dynamic light scattering, UV, and CD spectroscopic experimental methods. Its maximum magnetic moment per formula unit, in saturation field, is estimated to be 19.46 $\mu_B$, and persists from 277 to 330 K.

19 Claims, 5 Drawing Sheets

MOLECULAR MAGNETIC PROTEIN

BACKGROUND OF THE INVENTION

1. Field of the Invention

The present invention relates to molecular magnetic protein, in particular to a highly magnetically aligned metallothionin containing manganese and cadmium.

2. Description of the Related Art

Molecular magnets, for which we refer to organic or biological molecules bearing magnetic moments, offer new opportunity in the creation of novel, low dimensional, nano-structured materials. There have been emphases on those molecular magnets that operate at room temperatures or above (Petty, M C; Bryce, M R; Bloor, D. Introduction to Molecular Electronics; Edward Arnold: London, 1995).

Metallothionein (MT) plays a role of detoxication and serves as an antioxidant in mammalian. It spreads widely in many organs, but most frequently in the livers and the kidneys. MT is a thermally stable protein and contains 61 amino acid units. It has 20 conserved cysteines (Cys) with no disulfide bond detected (Eaton et al., Toxicology and Applied Pharmacology (1985) 78, 158–162,). In addition, its secondary structure contains no α-helix or β-sheet. These Cys' form two metal binding clusters located at the carboxyl (α-domain) and amino (β-domain) terminals of MT.

As evidenced from X-ray crystallography and solution NMR studies, the purified native metallothionein-2 (MT-2) from rabbit, contained seven metal ions (i.e., $Zn^{2+}/Cd^{2+}$) distributed in two metal clusters (see e.g., Robbins et al., J. Mol. Biol. (1991) 221, 1269–1293; Messerle et al., J. Mol. Biol. (1992) 225, 433–443). Four of the seven ions compose an $(M_4S_{11})^{3-}$ cluster in the α-domain, and the rest three compose an $(M_3S_9)^{3-}$ cluster in the β-domain, where M denotes metal ions ($Zn^{2+}$, $Cd^{2+}$, or others). (See e.g., Otvos et al., Proc. Natl. Acad. Sct. USA 77, 7094–7098 (1980); Boulange et al., Proc. Natl. Acad. Sci. USA, (1983) 80, 1501–1505; Chang et al., Protein Engineering (1996) 9, 1165–1172). These two ion-binding clusters located approximately three to four nanometers within each other (see Robbins et al., J. Mol. Biol. (1991) 221, 1269–1293) and have similar characteristics as the "semiconductor MS" compounds (see e.g., Wei et al., Physical Review Letters, (1986) 56, 2391–2394; Spaldin et al., Magnetic Materials. Fundamentals and Device Applications (2003)).

The inventors have now developed molecular magnets produced from metallothionein. To the inventors' knowledge, this is the first report on molecular magnet concerning biological systems that is functional at an operating temperature as high as 300 K.

SUMMARY OF THE INVENTION

The present invention provides a magnetically aligned metallothionein containing manganese and cadmium with a formula of $Mn_xCd_{7-x}MT$, wherein x=1 to 6. Preferably, each molecule of the metallothionein contains two atoms of manganese and five atoms of cadmium, i.e., x=2 in the formula of $Mn_xCd_{7-x}MT$. Per molecule of metallothionein has a maximum magnetic moment of about 18.6 $\mu_B$ in saturation filed and persists at a temperature of 277 K to 330K. The metallothionein is magnetic protein. It has a magnetic moment of about 311.4 emu/mol under a field of 0.2 T at a temperature of 277 K.

The present invention also provides a method of making a magnetically aligned metallothionein containing manganese and cadmium comprising:

Dissolving a raw metallothionein in an unfolding buffer solution to unfold the raw metallothionein and strip the metal ion contained in the raw metallothionein;

removing the metal ion and this unfolded metallothionein called apo-metallothionein;

adding manganese and cadmium into the folding solution; and refolding the unfolded apo-metallothionein.

The refolding step is preferably conducted by a stepwise quasi-static folding approach in different folding buffers.

The various features of novelty which characterize the invention are pointed out with particularity in the claims annexed to and forming a part of the disclosure. For a better understanding of the invention, its operating advantages, and specific objects attained by its use, reference should be had to the drawing and descriptive matter in which there are illustrated and described preferred embodiments of the invention.

BRIEF DESCRIPTION OF THE DRAWINGS

In the drawings:

FIG. 2 (b) shows spectrum of ultraviolet (UV) absorption of Mn, Cd-MT-2.

FIG. 2 (c) shows spectrum of circular dichroism (CD) of Mn, Cd-MT-2.

FIG. 3 (b) shows that Mn-MT-2 exhibits no clear magnetic hyeresis cycle at 277K.

FIG. 3 (c) shows that Zn-MT-2 exhibits no clear magnetic hysteresis cycle at 300 K.

DETAILED DESCRIPTION OF THE PRESENTLY PREFERRED EMBODIMENTS

Example

Figure 1:
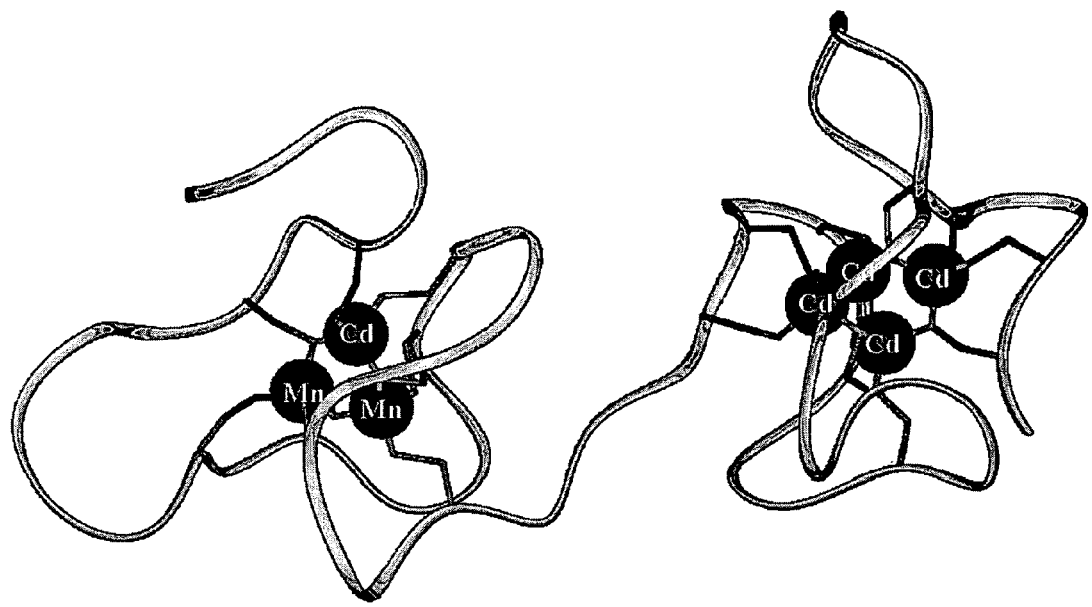
FIG. 1 shows molecular model of mixed $Cd^{2+}$, $Mn^{2+}$ Metallothionein-2 (Cd,Mn-MT-2).

The following example is given by way of illustration and not restrictive in any respect.

The Mn,Cd-MT-2 was obtained by the following procedures. A total of 5 mg of MT-2 (Sigma, St. Louis) was dissolved in 5 mL buffer solution at pH 11 to strip all metal ions (the buffers and procedures will be described in next paragraph). The free metal ions were removed by dialysis against the same buffer solution (de Naurois, M., et al., (1997) J. Appl. Phys. 81, 6120). The denatured MT-2 was refolded by the quasi-static-procedure, developed in our laboratory (de Naurois, M., et al., (1997) J. Appl. Phys. 81, 6120; Liu, Y. L., et al., (2003) Biochem. Biophys. Res. Comm. 306, 59) but with a minor modification. In addition to the basic constituents of buffer solution at pH 11 (de Naurois, M., et al., (1997) J. Appl. Phys. 81, 6120; Liu, Y. L., et al., (2003) Biochem. Biophys. Res. Comm. 306, 59), 10 µM $Mn^{2+}$ and 10 µM $Cd^{2+}$ were added in during the dialysis for removing urea. These two metal ion concentrations were increased to 1 mM when the pH was lowered to 6.8 (de Naurois, M., et al., (1997) J. Appl. Phys. 81, 6120). The excess $Mn^{2+}$ and $Cd^{2+}$ in the solution were removed after the MT-2 was folded back to its native form (de Naurois, M., et al., (1997) *J. Appl. Phys.* 81, 6120) again by dialysis to ensure that no free metal ions were present.

Native metallothionein was purchased from Sigma Ltd. (St. Louis, Mo.). All other chemicals were obtained from Merck Ltd. (Rahway, N.J.). The denaturing/unfolding buffer may contain urea and mannitol at a pH of above 10. In the present example, it contains 4.5 M urea with 10 mM Tris base (buffer salt), 0.1 M dithiothreitol (DTT) (anti-oxidation reagent and reduction reagent to break disulfide bonds of protein in high concentrations), 0.1% mannitol (chemical chaperonin) and 0.5 mM Pefabloc (protease inhibitor). There were five folding buffers employed in this study. Their compositions are summarized in the following chart.

| Folding Buffer | TRIS Base | pH | Urea | DTT | Mannitol | PEFABLOC | Mn/Cd 1:1 |
|---|---|---|---|---|---|---|---|
| 1 | 10 mM | 11 | 2M | 0.1 mM | 0.1% | 0.5 μM | 10 μM |
| 2 | 10 mM | 11 | 1M | 0.1 mM | 0.1% | 0.5 μM | 10 μM |
| 3 | 10 mM | 11 | | 0.1 mM | 0.1% | 0.5 μM | 10 μM |
| 4 | 10 mM | 8.8 | | 0.1 mM | 0.1% | 0.5 μM | 100 μM |
| 5 (the native buffer) | 10 mM | 8.8 | | 0.1 mM | | 0.5 μM | 100 μM |

Folding of MT by quasi-static-like thermal equilibrium dialysis.

The unfolded MT (U) was obtained by treating it with denaturing/unfolding buffer to make it 10 mg/L in concentration. This solution was left at room temperature for one hour and then was centrifuged at 4000 g for 30 min to remove the un-dissolved impurity. A quasi-static-like procedure involves five consecutive thermal equilibrium dialysis (TED) steps. Each of the folding intermediates is dialyzed against a particular folding buffer at 4° C.

Step 1: The unfolded MT (U) in denature/unfolding buffer was dialyzed against folding buffer 1 for 72 hr to dilute the urea concentration to 2 M (This produces intermediate 1 or $M_1$).

Step 2: $M_2$ was obtained by dialyzing $M_1$ against folding buffer 2 for 24 hr to dilute urea concentration to 1 M.

Step 3: $M_3$, an intermediate without denaturant (urea) in solution, was then obtained by dialyzing $M_2$ against folding buffer 3 for 24 hr.

Step 4: $M_3$ was further dialysed against folding buffer 4 for 24 hr, and the pH changed from 11 to 8.8 to produce $M_4$.

Step 5: Finally, the chemical chaperonin mannitol was removed by dialyzing $M_4$ against native buffer for 8 hr to yield $M_5$.

Figure 2:
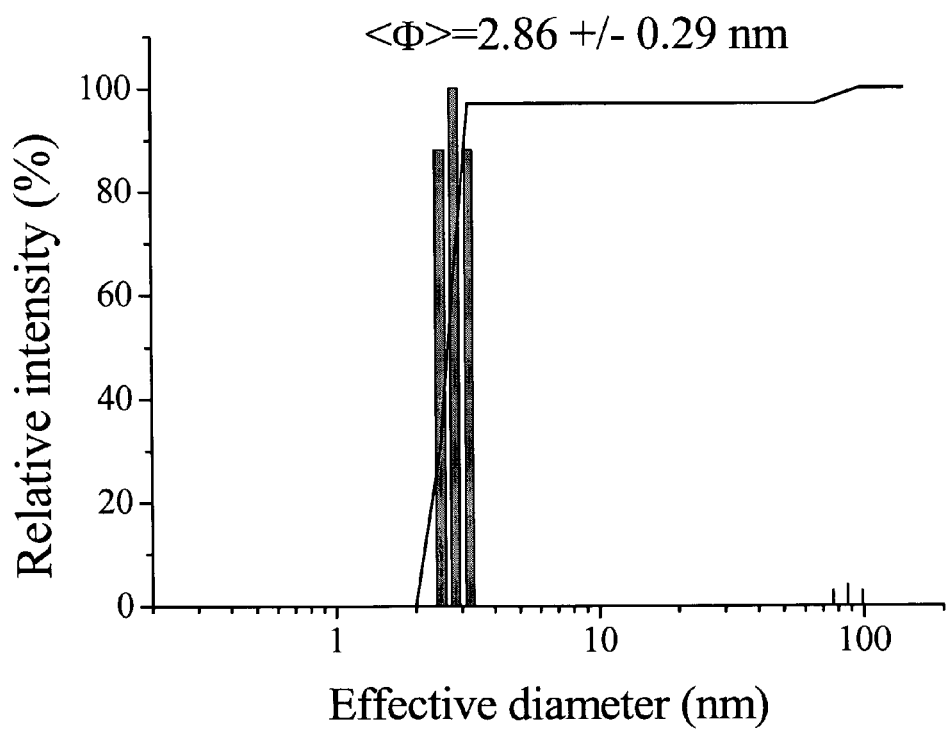
FIG. 2 (a) shows the spectrum of Mn,Cd-MT-2, measured by dynamic light scattering (DLS) spectrophotometer.
Figure 2B:
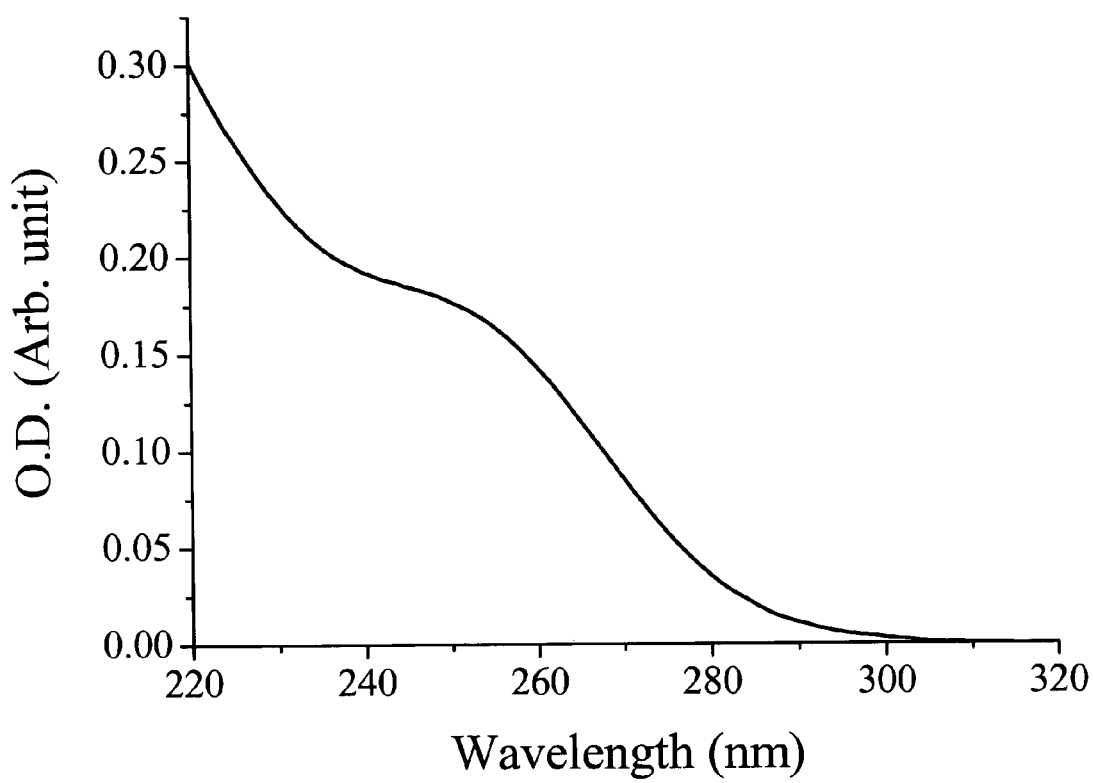
Figure 2C:
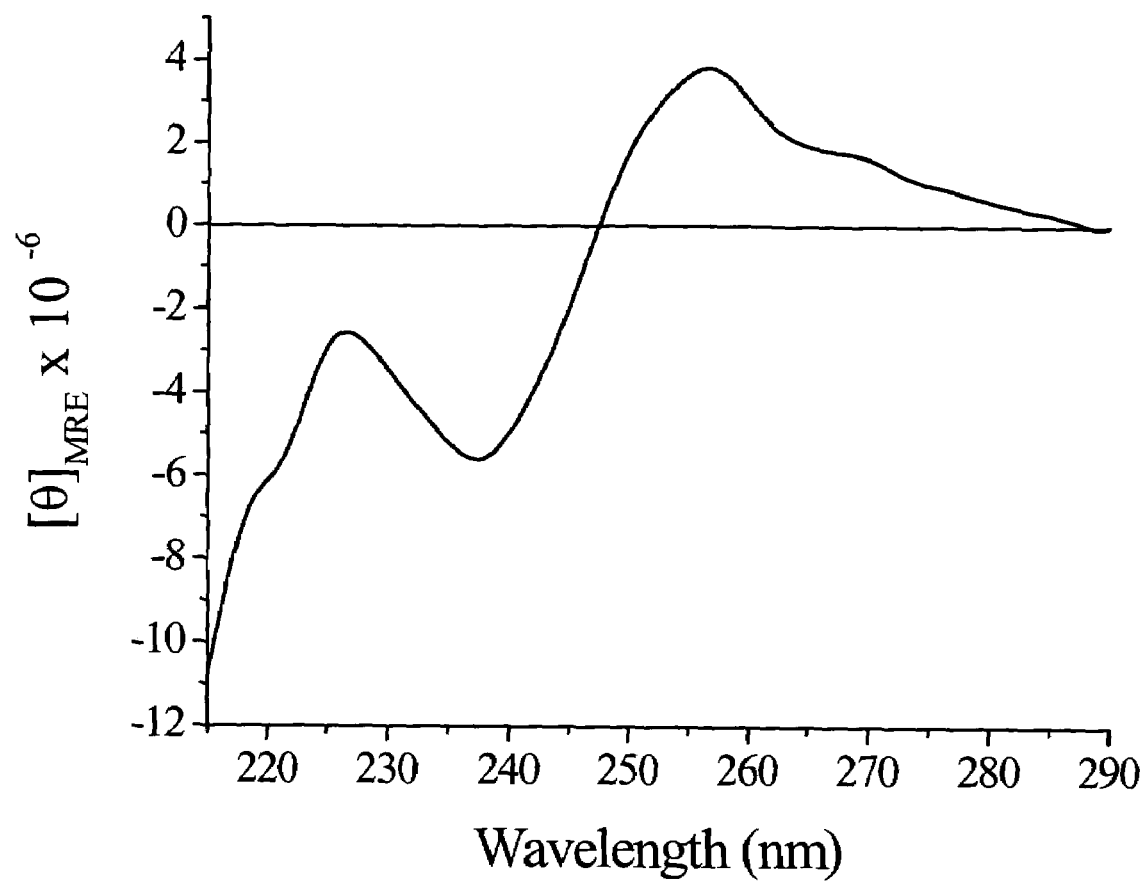

Results of atomic absorption spectroscopy showed that all Zn atoms have been substituted by two Mn and five Cd atoms. The effective diameter of Mn,Cd-MT-2, measured by dynamic light scattering (DLS) spectrophotometer, is around 3 nm—identical to the effective size of the native MT-2 (FIG. 2a). Additional evidence came from similar spectra of both the UV absorption and the circular dichroism (CD) (FIGS. 2b and 2c) to those of the native MT-2. These results indicated that the Mn,Cd-MT-2 was folded into its native conformation.

The binding sites of $Cd^{2+}$ and $Mn^{2+}$ in the clusters are fixed due to the preferential selection feature of metal ions (see Chang et al., Protein Engineering (1996) 9, 1165–1172). Therefore, without any intent to be bound by any mechanism, we propose that the two Mn ions are located in the β-domain of MT-2, i.e. the β metal binding cluster can be expressed as $(Mn_2CdS_3)^{3-}$ (see FIG. 1). FIG. 1 shows that the metal binding clusters are in "Zinc Blende" structure. The dark and light sticks denoted the carbon and sulfur atoms, respectively, of cysteine. The coil denoted the peptide backbone of MT-2. The α-cluster is on the right and β-on the left.

All $Mn^{2+}$ substituted MT-2 (designated as Mn-MT-2) was also synthesized and refolded as a control. The procedures were the same as those for Mn,Cd-MT-2 except only $Mn^{2+}$ was added into the dialysis buffer solutions.

Figure 3A:
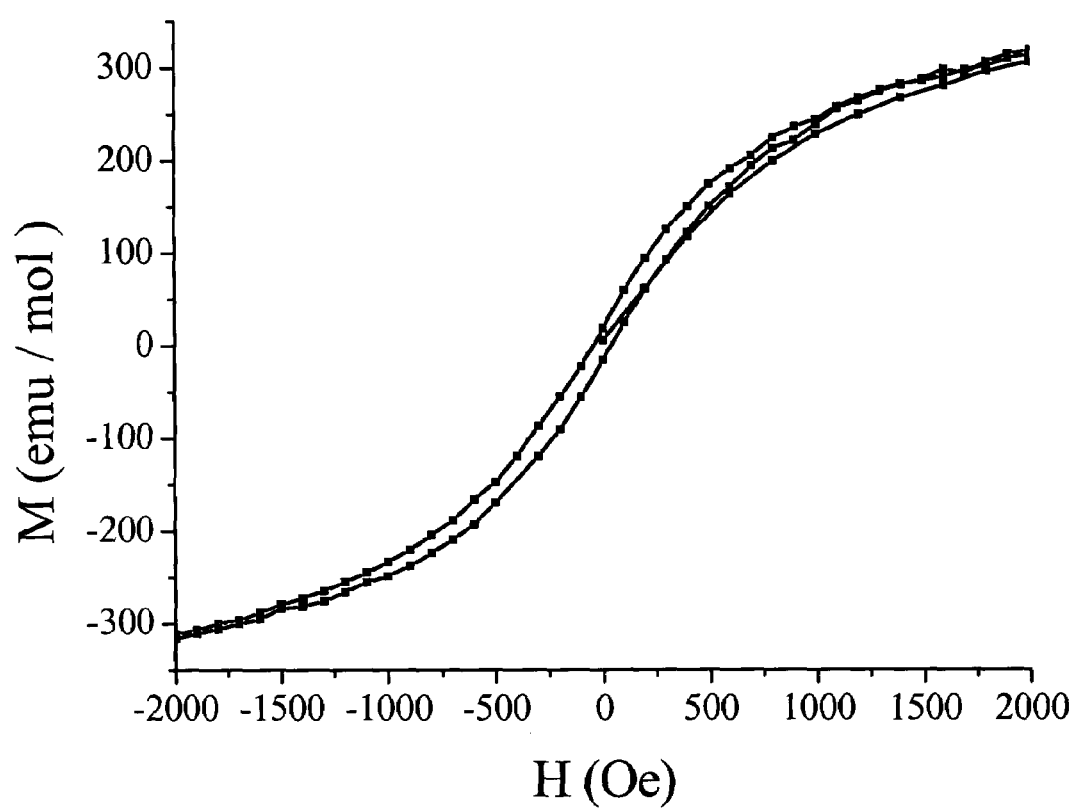
FIG. 3 (a) shows that Mn, Cd-MT-2 exhibits a clear magnetic hysteresis cycle at 277K.

The magnetic moment of Mn,Cd-MT-2 was measured on a lyophilized powder sample weighed 1.8 mg by a commercial SQUID magnetometer (Quantum Design, San Diego) in a sealed capsule from 277 to 330 K. By applying a cyclic external magnetic field between 3 Tesla and −3 Tesla, a clear magnetic hysteresis cycle was observed (FIG. 3). FIG. 3 shows the typical data at one temperature in the range studied (277 K) after subtracting a linear diamagnetic background. The magnetic moment of Mn,Cd-MT-2 was saturated at +/−0.2 T and the value of magnetic moment is about 311.4 emu/mol (emu, electron magnetic unit), the remanence was about 5% of the saturation and the coercive field was around 40 Oe (Oersteds). This indicates that the observed signal is ferromagnetic. Its magnetic moment changed within 4% (of 311.4 emu) between 277 and 330 K with a fluctuation of 0.3%. This result indicates that Mn,Cd-MT-2 not only holds a significant and detectable magnetic moment but also sustains it stably at room temperatures.

Figure 3B:
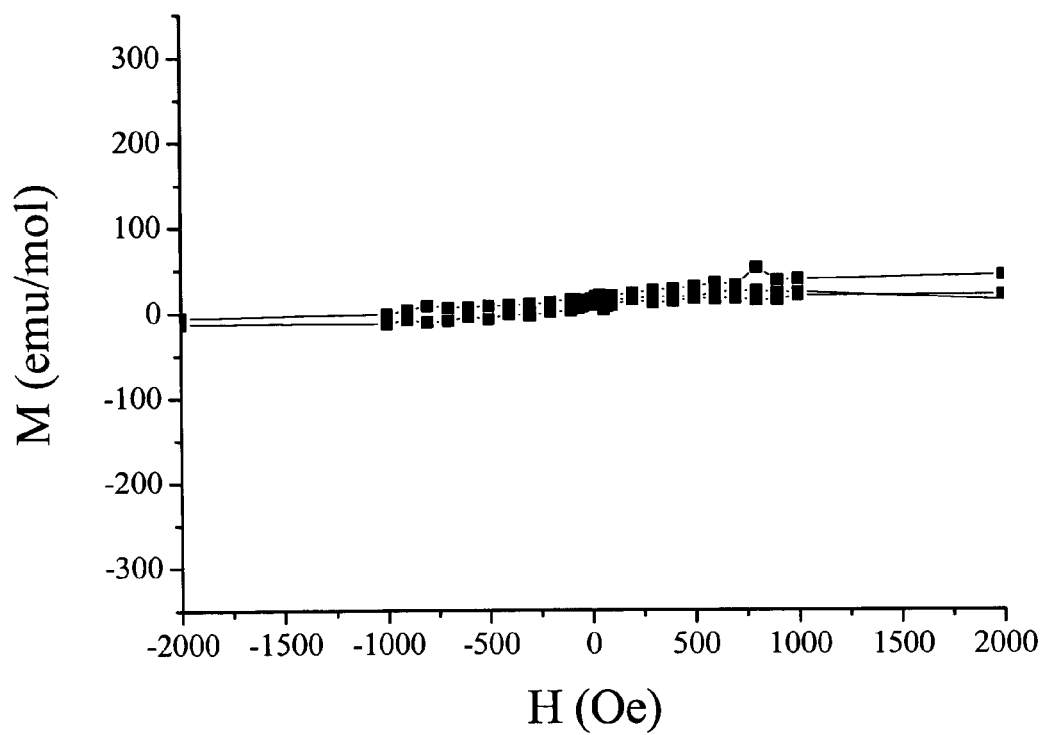
Figure 3C:
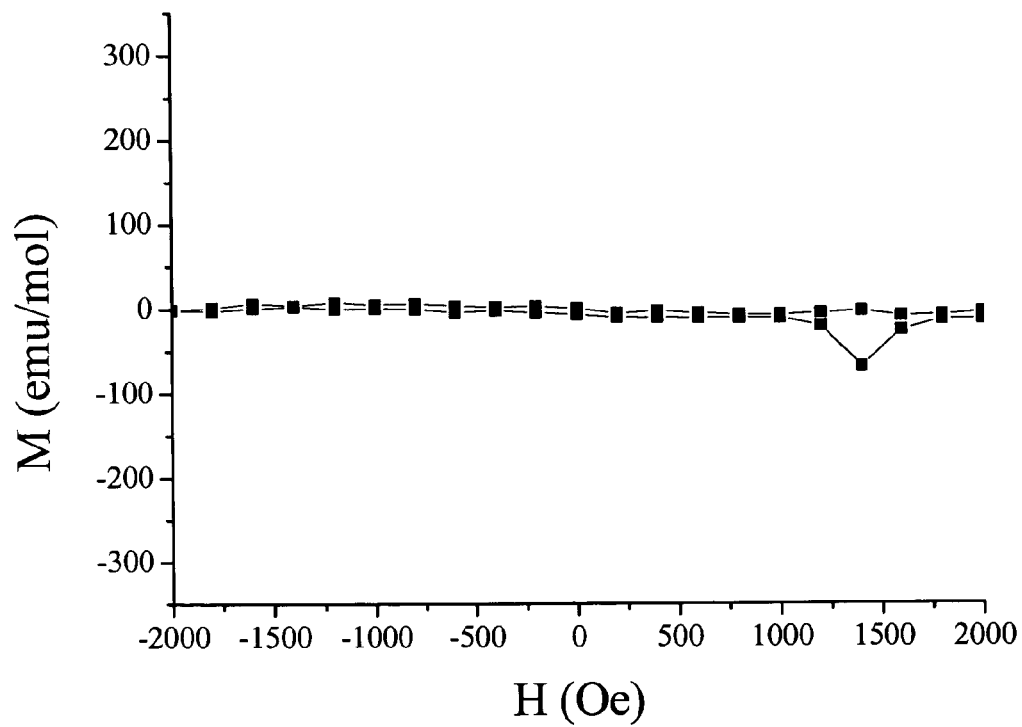

On the other hand, the solution containing only metal ions ($MnCl_2$ or $CdCl_2$, in 1 M concentration) as well as Mn-MT-2 or native MT-2 (Sigma) (1.8 mg MT's in all cases) exhibited no such hysteresis phenomenon (FIGS. 3b and 3c). These control experiments indicated that the magnetic property was originated from the structure of Mn,Cd-MT-2.

The error bar of each data point is smaller than the symbol size. The loops at 300 and 330 K are almost the same.

The super-exchange mechanism of spin correlation among magnetic ions and bridging ligands (i.e., sulfur (S), cerium (Ce), or tellurium (Te) atoms) is responsible for many of the magnetic properties in, e.g., magnetic insulators, the groups II/VI semiconductors, and other diluted magnetic semiconductors. (See e.g., Spaldin et al., Magnetic Materials. Fundamentals and Device Applications (2003)).

When the concentration of the substituting magnetic ions, such as $Mn^{2+}$, in a semiconductor, is higher, anti-ferromagnetism may result due to the alignment among the magnetic ions. However, the bridging ligands (i.e., sulfur atom, S) in double-exchange may result in ferromagnetism due to non-linear bond angles. This effect, which has been often used in constructing molecular magnets (Khanna, S. N., Castleman, A. W., Jr., (2003) *Quantum Phenomena in Clusters and Nanostructures*, (Springer-Verlag, Berlin)), would be enhanced in molecular nano-clusters.

The cluster behaves like a giant magnet with a combined moment from individual atoms (Khanna, S. N., Castleman, A. W., Jr., (2003) *Quantum Phenomena in Clusters and Nanostructures*, (Springer-Verlag, Berlin)). For example, $Mn_{12}O_{12}$-acetate nano-magnet exhibits ferromagnetic ordering with a total moment of 20 $\mu_B$ (Liu, Y. L., et al., (2003) *Biochem. Biophys. Res. Comm.* 306, 59; Khanna, S. N., Castleman, A. W., Jr., (2003) *Quantum Phenomena in Clusters and Nanostructures*, (Springer-Verlag, Berlin)), where $\mu_B$ is the magnetic moment of electron.

In case of Mn,Cd-MT-2, the magnetic moment may be caused by $(Mn_2CdS_3)^{3-}$ clusters embedded in the β-domain. Although the α-domain and Cd ions are non-magnetic, they may play an important role in stabilizing the structure of $(Mn_2CdS_3)^{3-}$, which makes the overall cluster magnetic. Therefore, the peptide chain of MT-2 may play a role as bridging ligand to align magnetic moments within the clusters so that the resulting magnetic moment may be even stronger than those in the magnetic semiconductors.

The magnetic moment of the cluster is equal to $Nng_e\mu_B$, where N and n are the total number and the effective number of unpaired electrons of magnetic atoms in the cluster, respectively; $g_e$ is the g factor of electrons ($g_e=2$). In the case of perfect alignment, the cluster $(Mn_2CdS_3)^{3-}$ may have a magnetic moment of 20 $\mu_B$. The average induced magnetization for a cluster smaller than a typical magnetic domain is equal to $(B\mu_B)/(3\ kT)(Nng_e)^2$ (de Naurois, M., et al., (1997) *J. Appl. Phys.* 81, 6120), where B is the strength of an applied magnetic field and k is the Boltzmann constant. In our case, the magnetization Mn,Cd-MT-2 was measured as 311.4 emu/mol under a field of 0.2 T at 277 K. Therefore, $Nng_e$ of Mn,Cd-MT-2 equals to 18.6 $\mu_B$, indicating a highly ordered alignment of magnetic moments as compared to a perfect 20 $\mu_B$. However, we shall admit that this is the first study of this new magnetic protein, therefore, the detailed molecular mechanism of its magnetic property needs further study.

In summary, we have successfully constructed a molecular magnet, Mn,Cd-MT-2, which is stable around room temperature. The observed magnetic moment may be explained by the highly ordered alignment of $(Mn_2CdS_9)^{3-}$ clusters embedded in the β-domain, attributable to peptide backbone serving as a key bridging ligand. More importantly, by using the quasi-static folding process a high purity and quantity Mn,Cd-MT-2 was obtained and it showed an activity similar to native metallothionein. Thus, the unique features of molecular magnetism and bio-compatibility make it a good candidate for biological applications and sensing sources of nano-devices, such as high density magnetic array, SPM magnetic protein probes and room temperature spintronic devices.

The invention is not limited by the embodiments described above which are presented as examples only but can be modified in various ways within the scope of protection defined by the appended patent claims.

All the references cited herein are explicitly incorporated as reference of the present application.

We claim:

1. A magnetically aligned metallothionein (MT) containing manganese(Mn) and cadmium (Cd) with a formula of $Mn_xCd_{7-x}MT$, wherein x=1 to 6.

2. The metallotionein of claim 1 wherein x is 2.

3. The metallothionein of claim 1, wherein said metallothionein has a maximum magnetic moment of about 311.4 emu/mol in saturation field and persists at a temperature range of 277 K to 330K.

4. The metallothionein of claim 1 being ferromagnetic.

5. The metallothionein of claim 1 having a magnetic moment of about 311.4 emu/mol under a field of 0.2T at a temperature of 277 K.

6. The metallothionein of claim 4 having a remanence of about 5%.

7. The metallothionein of claim 4 having a coercive field of about 40 Oe.

8. The metallothionein of claim 4 wherein the magnetic moment changes within 4% of 311.4 emu/mol with a fluctuation of 0.3% between the temperatures of 277 K and 330 K.

9. A method of making a magnetically aligned metallothionein containing manganese and cadmium comprising: dissolving a raw metallothionein in an unfolding buffer solution to unfold the raw metallothionein and strip metal ions contained in the raw metallothionein; removing metal ions; adding manganese and cadmium ions to the unfolded metallothionein; and refolding the unfolded metallothionein.

10. The method of claim 9 further comprising a step of removing the excess manganese and cadmium ions from the metallothionein solution following the refolding step.

11. The method of claim 9 wherein the unfolding buffer solution contains urea and mannitol at a pH of above 10.

12. The method of claim 9 wherein the raw metallothionein is native metallothionein.

13. The method of claim 11 wherein the unfolding buffer solution contains 4.5 M urea, 10 mM TRIS, 0.1 M DTT, 0.1% mannitol, and 0.5M PEFABLOC at a pH of 11.

14. The method of claim 9 wherein the refolding step is conducted by a stepwise thermal equilibrium dialysis approach in different folding buffers.

15. The method of claim 14 wherein the stepwise thermal equilibrium dialysis approach comprises first removing the urea and then removing the mannitol from the metallothionein solution.

16. The method of claim 14 wherein at least one of the folding buffers for refolding the unfolded metallothionein comprises the manganese and cadmium ions.

17. The method of claim 16 wherein the concentration of manganese is the same as the concentration cadmium in the different folding buffers.

18. The method of claim 14 wherein the stepwise thermal equilibrium dialysis approach comprises five consecutive thermal equilibrium dialysis steps respectively conducted in folding buffer 1 (10 mM Tris-base, 2M urea, 0.1 mM DTT, 0.1% mannitol, and 0.5 μM PEFABLOC in a pH of 11), folding buffer 2 (10 mM Tris-base, 1 M urea, 0.1 mM DTT, 0.1% mannitol, and 0.5 M μM PEFABLOC in a pH of 11), folding buffer 3(10 mM Tris-base, 0.1 mM DTT, 0.1% mannitol, and 0.5 μM PEFABLOC in a pH of 11), folding buffer 4(10 mM Tris-base, 0.1 mM DTT, 0.1% mannitol, and 0.5 μM PEFABLOC in a pH of 8.8), and folding buffer 5(10 mM Tris-base, 0.1 mM DTT, and 0.5 μM PEFABLOC in a pH of 8.8).

19. A magnetically aligned metallothionein made by the method of claim 9.

* * * * *